United States Patent [19]
Julius

[11] Patent Number: 5,880,286
[45] Date of Patent: Mar. 9, 1999

[54] ACETYLATION OF STERICALLY HINDERED DIAMINES

[75] Inventor: Manfred Julius, Limburgerhof, Germany

[73] Assignee: BASF Aktiengesellschaft, Ludwigshafen, Germany

[21] Appl. No.: 955,260

[22] Filed: Oct. 21, 1997

[30] Foreign Application Priority Data

Oct. 28, 1996 [DE] Germany ............... 19644806.9

[51] Int. Cl.⁶ ............... C07D 211/58; C07D 207/14
[52] U.S. Cl. ............... 546/244; 548/557; 540/605
[58] Field of Search ............... 546/244; 548/557; 540/605

[56] References Cited

U.S. PATENT DOCUMENTS

| | | |
|---|---|---|
| 3,904,581 | 9/1975 | Murayama et al. ............... 260/45 |
| 4,326,067 | 4/1982 | Fazio ............... 548/347 |

FOREIGN PATENT DOCUMENTS

| | | |
|---|---|---|
| 389 419 | 9/1990 | European Pat. Off. . |
| 2349962 | 10/1973 | Germany . |
| 3901246 | 1/1989 | Germany . |

OTHER PUBLICATIONS

C. Harries, *Liebigs Ann. Chem.*, 417, 1918, pp. 118–125.

E.G. Rozantsev, *Izv. Akad. Nank. SSSR*, Ser. Khim 8, 1966, pp. 1422–1423.

*Primary Examiner*—Alan L. Rotman
*Assistant Examiner*—Charanjit S. Aulakh
*Attorney, Agent, or Firm*—Keil & Weinkauf

[57] ABSTRACT

A process for acetylating diamines having a sterically hindered amino function and a further, sterically unhindered amino function where the acetylation takes place at the sterically unhindered amino function is provided comprises reacting the diamine with ketene. A preferred diamine is 4-amino-2,2,6,6-tetramethylpiperidine (TAD).

5 Claims, No Drawings

ACETYLATION OF STERICALLY HINDERED DIAMINES

The present invention relates to a process for acetylating diamines having a sterically hindered amino function and a further, sterically unhindered amino function where the acetylation takes place at the sterically unhindered amino function.

Amides are known to be prepared by reacting amines with ketene [Houben Weyl, Volume VII/4 (1968), p. 124–126]. It is a disadvantage of this reaction that the ketene, owing to its high reactivity, also reacts with sterically hindered secondary amino functions, as described in the prior application DE-A 196 34 147.

Amines are also known to be acetylated by reaction with acetic anhydride, with concomitant formation of an equimolar amount of acetic acid as by-product. This applies in particular to the preparation of 4-acetamido-2,2,6,6-tetramethylpiperidine, cf. 1) C. Harries, Liebigs Ann. Chem. 417 (1918), 120–121; 2a) E. G. Rozantsev in H. Ulrich, Free Nitroxyl Radicals, p. 231, Plenum, London (1979); 2b) E. G. Rozantsev et al., Izv. Akad. Nauk SSSR, Ser. Khim. 8 (1966), 1477–1479; = Bull. Acad. Sci USSR, Div. Chem. Sci. 15 (1966), 1422–1423; 3) N. R. Plessas et al., Carbohydr. Res. 89 (1981), p. 219; 4) EP-B 0 389 419, p. 20, lines 45–55 (Ciba-Geigy, 1990).

In addition, acetylated amino groups can also be prepared by reaction with acetyl chloride, with release of a molar equivalent of hydrogen chloride (DE-A 39 01 246, DE-A 23 49 962).

A further acetylation method, in particular for acetylating diamines having a sterically hindered amino function and a further, sterically unhindered amino function at the latter, is the reduction of a nitroxyl radical, for example 4-acetamido-2,2,6,6-tetramethylpiperidin-1-oxyl, with iron carbonyls or other reducing agents, cf. H. Alper, J. Org. Chem. 38 (1973), 1417–1418.

It is a disadvantage of the above-described reaction of amines with acetic anhydride for preparing acetamides that, in the reaction with acetic anhydride, one molar equivalent of acetic acid is formed as co-product. Initially, this forms an ammonium acetate salt. In the known process, it is therefore necessary to free the amine in a further step by reacting the salt with at least a stoichiometric amount of a base, for example aqueous sodium hydroxide.

Alternatively, the acetic acid, or else the acetic anhydride which is in most cases employed in excess, can be removed by distillation.

The other processes mentioned above are also either complicated or not without ecological risks.

An additional problem is the insufficient selectivity of the known processes for acetylating diamines having a sterically hindered amino function and a further, sterically unhindered amino function.

It is an object of the present invention to provide a process for acetylating diamines having a sterically hindered amino function and a further, sterically unhindered amino function where the acetylation takes place at the sterically unhindered amino function.

We have found that this object is achieved by a process for acetylating diamines having a sterically hindered amino function and a further, sterically unhindered amino function where the acetylation takes place at the sterically unhindered amino function by reacting the diamine with ketene.

The term "sterically hindered amino function" is employed for amino functions carrying more than one substituent which is branched in α-position to the amino function. The sterically hindered amino function can be part of a heterocyclic ring system. In 4-amino-2,2,6,6-tetramethylpiperidin (TAD), the methyl substitution in 2- and 6-position of the ring causes sterical hinderance of the secondary amine function. By contrast, the primary amino function in 4-position is a sterically unhindered amino function.

The process according to the invention is carried out under very mild reaction conditions. In particular, the reaction temperature is in the range of from $-30°$ C. to $65°$ C. Furthermore, the selectivity of the process according to the invention is increased by carrying out the reaction in an aprotic solvent, particularly in tetrahydrofuran.

The process is preferably carried out without catalysis, although it is also possible to employ catalysts, such as trialkylamines or 4-dimethylaminopyridine (DMAP).

Suitable solvents for carrying out the reaction are polar or nonpolar, inert, aprotic organic solvents, such as hydrocarbons or ethers. Preference is given to ethers, in particular tetrahydrofuran. If appropriate, the reaction can also be carried out without a solvent. The process according to the invention is particularly preferably employed for acetylating diamines having a sterically hindered amino function and a further, sterically unhindered amino function where the sterically hindered amino function is part of an N-heterocycle. The N-heterocycle is in particular 4-amino-2,2,6,6-tetramethylpiperidine (TAD). TAD is an important intermediate in the synthesis of hindered amine light stabilizers (HALS). In the very particularly preferred reaction of TAD with ketene, the sterically unhindered amino function is acetylated with the ketene with a selectivity of over 95%, although the ketene is known to react with sterically hindered amino functions under normal conditions, owing to its high reactivity. The reaction of TAD with ketene according to the invention is preferably carried out at atmospheric pressure and/or batch-wise, although the reaction may also be carried out in an autoclave under superatmospheric pressure, and continuously.

The following example illustrates the process according to the invention:

EXAMPLE

Synthesis of 4-acetamido-2,2,6, 6-tetramethylpiperidine

Under $N_2$ and at $0°$ C., a 0.5 l four-neck flask was charged with a solution of 46.88 g (0.30 mol) of 4-amino-2,2,6,6-tetramethylpiperidine (TAD) (purity according to GC: 98.8% by area) in 250 ml of dry tetrahydrofuran (THF). A stream of ketene gas of about 0.5 mol/h was passed into the stirred solution over 1.5 h, during which the temperature of the reaction mixture was kept at from $+1°$ to $-2°$ C. (cooling bath) and the color of the solution changed from light yellow to brown. The TAD conversion was 100% and the selectivity 95.3% (according to GC; conditions: 30 m RTX-5-Amine; $50°-250°$ C., $5°$ C./min). The reaction product was concentrated at 100-20 mbar and $50°$ C. using a rotary evaporator, and the residue was recrystallized from about 70 g of ethanol. The product was filtered off under suction, washed with about 100 ml of petroleum ether 30/75 and dried at 0.5 mbar and $22°$ C. Yield: 36.2 g (61.1%) of light-yellow crystals. Purity according to GC: 99.2% Mp.: $119°-120°$ C.

A further 11.4 g (19.0%) of the product having a purity of 97.7% (GC) were crystallized from the mother liquor.

The total yield of isolated product was 80.1% (calculated for a product of 100% purity).

$^{13}C$ NMR (62.9 MHz, $CDCl_3$): δ=23.32 (q; $CH_3$—CO), 28.23 (q; 2.$CH_3$), 34.65 (q; 2.$CH_3$), 42.39 (d; CH—N), 44.95 (t; 2.CH$_2$—CH), 51.27 (s; 2.C(CH$_3$)$_2$), 169.84 (s; C=O). Mass spectrum (EI): M$^+$=198. IR spectrum: 1640 and 1560 cm$^{-1}$ (secondary amide).

We claim:

1. A process for acetylating diamines having a sterically hindered amino function, said sterically hindered amino function being an amino function carrying four methyl group in the α-position to the amino function, said sterically hindered amino function being part of a 5–7-membered heterocyclic ring system, and a further, sterically unhindered amino function where acetylation takes place at the sterically unhindered amino function, which process comprises reacting the diamine with ketene.

2. A process as claimed in claim 1, wherein the reaction is carried out at from −30° C. to 65° C.

3. A process as claimed in claim 1, wherein the reaction is carried out in an aprotic solvent.

4. A process as claimed in claim 3, wherein the reaction is carried out in tetrahydrofuran.

5. A process as claimed in claim 1, wherein the diamine is 4-amino2,2,6,6-tetramethylpiperidine (TAD).

* * * * *